(12) United States Patent
Li et al.

(10) Patent No.: US 11,109,843 B2
(45) Date of Patent: Sep. 7, 2021

(54) ULTRASONIC IMAGE PICKUP DEVICE AND IMAGE PROCESSING DEVICE

(71) Applicant: Hitachi, Ltd., Tokyo (JP)

(72) Inventors: Zisheng Li, Tokyo (JP); Tsuneya Kurihara, Tokyo (JP); Yasuhiro Akiyama, Tokyo (JP)

(73) Assignee: HITACHI, LTD., Tokyo (JP)

( * ) Notice: Subject to any disclaimer, the term of this patent is extended or adjusted under 35 U.S.C. 154(b) by 784 days.

(21) Appl. No.: 15/552,502

(22) PCT Filed: Nov. 27, 2015

(86) PCT No.: PCT/JP2015/083482
§ 371 (c)(1),
(2) Date: Aug. 22, 2017

(87) PCT Pub. No.: WO2016/136065
PCT Pub. Date: Jan. 9, 2016

(65) Prior Publication Data
US 2018/0028157 A1    Feb. 1, 2018

(30) Foreign Application Priority Data
Feb. 26, 2015 (JP) .............................. JP2015-037353

(51) Int. Cl.
*A61B 8/08* (2006.01)
*G06T 7/33* (2017.01)
(Continued)

(52) U.S. Cl.
CPC ............ *A61B 8/5261* (2013.01); *A61B 5/055* (2013.01); *A61B 6/03* (2013.01); *A61B 6/032* (2013.01);
(Continued)

(58) Field of Classification Search
None
See application file for complete search history.

(56) References Cited

U.S. PATENT DOCUMENTS 8,226,560 B2    7/2012  Arai et al.
8,340,374 B2   12/2012  Yamagata
(Continued)

FOREIGN PATENT DOCUMENTS

CN    101455576 A    6/2009
JP    2008-188417 A  8/2008
(Continued)

OTHER PUBLICATIONS

Extended European Search Report received in corresponding European Application No. 15883355.8 dated Jun. 29, 2018.
(Continued)

*Primary Examiner* — Angela M Hoffa
*Assistant Examiner* — Younhee Choi
(74) *Attorney, Agent, or Firm* — Mattingly & Malur, PC

(57) ABSTRACT

Alignment of an ultrasonograph and volume data obtained beforehand is correctly performed without requiring a user to perform complicated operation. First volume data for an ultrasonograph and second volume data obtained by another imaging apparatus are received and aligned. A predetermined imaging part selected from a plurality of imaging parts of a subject is received from a user. The second volume data are initially rotated by a rotation angle corresponding to the imaging part received by the receptor, and alignment of the initially rotated second volume data and the first volume data after is further carried out.

8 Claims, 15 Drawing Sheets

(51) Int. Cl.
*A61B 8/00* (2006.01)
*A61B 8/14* (2006.01)
*A61B 6/03* (2006.01)
*A61B 5/055* (2006.01)

(52) U.S. Cl.
CPC .............. *A61B 8/0891* (2013.01); *A61B 8/14* (2013.01); *A61B 8/4254* (2013.01); *A61B 8/463* (2013.01); *A61B 8/5207* (2013.01); *G06T 7/33* (2017.01); *A61B 8/0883* (2013.01); *A61B 8/4416* (2013.01); *G06T 2207/10072* (2013.01); *G06T 2207/10088* (2013.01); *G06T 2207/30056* (2013.01); *G06T 2207/30101* (2013.01)

(56) References Cited

U.S. PATENT DOCUMENTS

| | | | | |
|---|---|---|---|---|
| 8,369,597 | B2* | 2/2013 | Hyun | A61B 5/04284 |
| | | | | 382/131 |
| 2003/0018245 | A1* | 1/2003 | Kaufman | A61B 6/463 |
| | | | | 600/407 |
| 2007/0010743 | A1 | 1/2007 | Arai | |
| 2008/0298660 | A1 | 12/2008 | Yamagata | |
| 2010/0239150 | A1* | 9/2010 | Ishikawa | A61B 5/0095 |
| | | | | 382/131 |
| 2012/0179040 | A1 | 7/2012 | Arai et al. | |
| 2012/0184851 | A1 | 7/2012 | Arai et al. | |
| 2012/0184852 | A1 | 7/2012 | Arai et al. | |
| 2012/0253171 | A1* | 10/2012 | Ishikawa | G06T 7/33 |
| | | | | 600/411 |
| 2013/0226003 | A1* | 8/2013 | Edie | G06T 7/0012 |
| | | | | 600/454 |
| 2014/0193053 | A1 | 7/2014 | Kadoury et al. | |
| 2014/0321726 | A1* | 10/2014 | Shin | G06T 7/32 |
| | | | | 382/131 |

FOREIGN PATENT DOCUMENTS

| | | |
|---|---|---|
| JP | 2011-011001 A | 1/2011 |
| JP | 2011-167331 A | 9/2011 |
| JP | 2014-195729 A | 10/2014 |
| WO | 2004/098414 A1 | 11/2004 |

OTHER PUBLICATIONS

Schlosser, J et al., "Automatic 3D Ultrasound Calibration for Image Guided Therapy Using Intramodality Image Registration", Physics in Medicine and Biology, Oct. 8, 2013, pp. 7481-7496, vol. 58, No. 21.

International Search Report of PCT/JP2015/083482 dated Feb. 2, 2016.

Chinese Office Action received in corresponding Chinese Application No. 201580072590.1 dated Aug. 5, 2019.

International Preliminary Report on Patentability received in corresponding International Application No. PCT/JP2015/083482 dated Sep. 8, 2017.

* cited by examiner

14 Foot switch

| Specified zone | Rotation angle (degree) | | | Parallel translation (mm) | | |
|---|---|---|---|---|---|---|
| | X | Y | Z | X | Y | Z |
| $S_1$ | 20.21 | -15.38 | 51.23 | 25.39 | -34.98 | 70.41 |
| $S_2$ | -35.35 | 11.26 | -85.67 | -15.88 | 56.24 | -68.59 |
| ⋮ | ⋮ | ⋮ | ⋮ | ⋮ | ⋮ | ⋮ |
| $S_8$ | 19.77 | -36.89 | 65.33 | 65.21 | -14.25 | -23.64 |

Ultrasonic blood vessel data

CT blood vessel data (A)

(B)

Initially rotated CT blood vessel data (C)

(A)                          (B)

ULTRASONIC IMAGE PICKUP DEVICE AND IMAGE PROCESSING DEVICE

TECHNICAL FIELD

The present invention relates to an ultrasonic imaging apparatus, in particular, an ultrasonic imaging apparatus that can simultaneously display an ultrasonograph acquired in real time, and an image of the same section obtained from volume data obtained beforehand with another imaging apparatus.

BACKGROUND ART

Ultrasonic imaging apparatuses irradiate ultrasonic waves on a subject and form an image of an internal structure of the subject from reflection signals of the waves. Therefore, they enable non-invasive and real-time observation of a patient.

On the other hand, other medical imaging apparatuses such as X-ray CT (Computed Tomography) apparatuses and MRI (Magnetic Resonance Imaging) apparatuses enable imaging of a wide area with high resolution, and therefore fine lesions or relationship of internal organs can be easily grasped with them. For example, tumors such as liver cancer can be found in an MRI image or an X-ray CT image at an early stage.

Patent document 1 discloses a diagnostic imaging system that obtains an ultrasonograph of an arbitrary section with an ultrasound probe having a position sensor, constructs a two-dimensional image of the corresponding section from volume data of the same subject obtained beforehand with another medical imaging apparatus, and displays both the images side by side. In this technique, a two-dimensional image of a current position of the ultrasound probe is constructed in real time from volume data obtained beforehand with another medical imaging apparatus. Therefore, it is necessary to perform a processing for matching the position of the ultrasonograph and the corresponding position in the volume data beforehand. Patent document 1 discloses a procedure for matching the positions. First, a user such as medical practitioner manually moves an ultrasound probe on a subject to search for a position where an ultrasonograph including a disease part suitable as an alignment image can be obtained. Then, the user selects a position of the disease part and a position of a characteristic structure other than the disease part on the ultrasonograph obtained by the search. The user further specifies a position corresponding to the position of the disease part and a position of the characteristic structure of the ultrasonograph on an image of volume data obtained with another medical imaging apparatus by manually using a mouse or the like. The diagnostic imaging system aligns the volume data so that the two positions on the ultrasonograph selected by the user and the two positions specified on the image obtained with the other medical imaging apparatus match with each other.

PRIOR ART REFERENCES

Patent Document

Patent document 1: Japanese Patent Unexamined Publication (KOKAI) No. 2008-188417

SUMMARY OF THE INVENTION

Object to be Achieved by the Invention

However, according to the technique of Patent document 1, in order to carry out alignment of the ultrasonograph and the volume data obtained with another medical imaging apparatus, a user such as medical practitioner must carry out a plurality of the complicated manual operations of manually moving an ultrasound probe to search for a position of the ultrasonograph suitable as an alignment image, manually selecting a plurality of positions on the ultrasonograph, and further specifying a plurality of corresponding positions on the image of volume data. These complicated manual operations for the alignment not only impose heavy burdens on the user who is a medical practitioner, but also impose heavy burdens on the subject being waited on a bed during the manual operations for the alignment with being applied with the ultrasound probe. Further, since the position used as the basis of the alignment consists of two positions on one ultrasonograph, highly precise three-dimensional alignment is difficult.

Further, although the technique described in Patent document 1 supposes use thereof with a treatment or surgical operation not accompanied by abdominal incision of the subject such as radio-frequency ablation (RFA), it is desired in recent years to directly put an ultrasound probe on an internal organ of a subject in an abdominally incised state and thereby confirm a region to be operated such as tumors with an ultrasonograph and a corresponding MRI image or CT image of high resolution during the surgical operation. Therefore, it is desired to avoid as much as possible that the user such as medical practitioner touches a switch, mouse, or the like of an input device with the hand for the alignment of the volume data during the operation. It is also desired to perform the alignment of the volume data in a short time as much as possible, in order to reduce the burden imposed on the subject in an abdominally incised state. Furthermore, in order to correctly confirm positions of tumor or the like on an ultrasonograph, exact alignment of the volume data of high resolution and the ultrasonograph is desired.

An object of the present invention is to provide an ultrasonic imaging apparatus that enables correct alignment of an ultrasonograph and volume data obtained beforehand without requiring complicated operations of users.

Means for Achieving the Object

The ultrasonic imaging apparatus of the present invention comprises an ultrasound probe that transmits a ultrasonic wave to a subject and receives a ultrasonic wave from the subject, a position sensor attached to the ultrasound probe, an image generator that generates an ultrasonograph from a signal received by the ultrasound probe and generates first volume data from the ultrasonograph and positional information of the ultrasound probe obtained from the position sensor, and an image processing device that receives second volume data obtained for the subject by another external imaging apparatus and processes them. The image processing device is provided with an aligner that carries out alignment of the first volume data and the second volume data. The aligner comprises a receptor that receives a predetermined imaging part selected from a plurality of imaging parts of a subject from a user, and a rotation processor. The rotation processor initially rotates the second volume data by a rotation angle corresponding to the imaging part that is received by the receptor, and further carries out alignment of the initially rotated second volume data and the first volume data.

Effect of the Invention

According to the present invention, alignment of ultrasonic volume data and volume data obtained with another imaging apparatus can be automatically and correctly carried out.

BRIEF DESCRIPTION OF THE DRAWINGS

FIG. 5 A table showing relation between zones of internal organ and rotation angles of CT image according to the embodiment 1.

MODES FOR CARRYING OUT THE INVENTION

Figure 1:
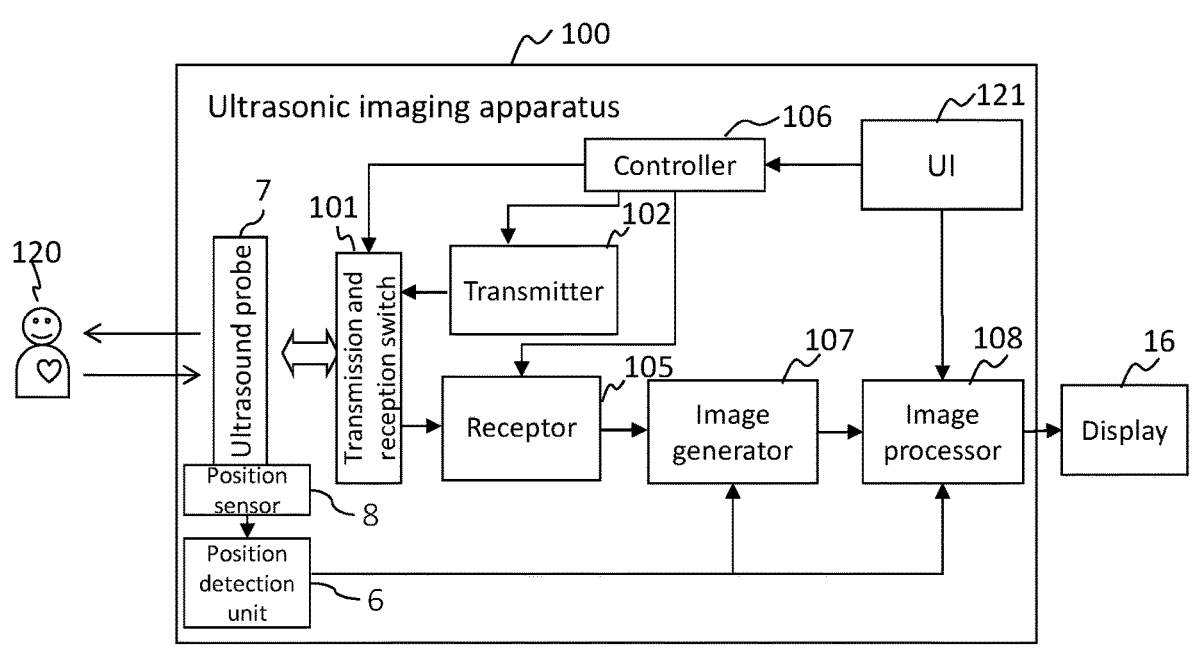
FIG. 1 A block diagram showing the whole configuration of the ultrasonic imaging apparatus of the embodiment 1.

Hereafter, embodiments of the present invention will be explained in detail with reference to the drawings. In all of the drawings for explanation of the embodiments, the same parts are indicated with the same numerals in principle, and repetitive explanations thereof are omitted.

<Principle and Outline>

The inventors of the present invention considered that the cause of the complicated operations for the alignment of ultrasonograph and volume data is that imaging direction and view of ultrasonic imaging apparatus are greatly different from those of other medical imaging apparatuses such as MRI and X-ray CT apparatuses. It is difficult to apply a general automatic alignment procedure to alignment of images of greatly different imaging directions and views. Therefore, according to the present invention, an initial rotation processing is carries out according to type of imaging region so that imaging directions of ultrasonograph and image obtained with another medical imaging apparatus coincide to each other, and the automatic alignment procedure can be applied to them.

When an ultrasonic imaging apparatus is used, while an ultrasound probe is moved along a body surface of a subject or surface of internal organ of an abdominally incised subject, ultrasonic waves are transmitted from the ultrasound probe to the subject to scan the subject, reflection waves are received, and an image is obtained from them. Therefore, when the body surface or surface of internal organ of the subject is curving, the ultrasound probe inclines along the curved surface, and there is obtained an ultrasonograph of a surface for which signals are transmitted and received with the ultrasound probe applied to the surface at the inclination angle. Further, when a user who is a medical practitioner desires to see an ultrasonograph of a direction having a desired angle corresponding to a certain structure in an internal organ, the user may incline the ultrasound probe by the desired angle. Furthermore, when, for example, the longitudinal direction of internal organ is slanting to the body axis, a user may successively obtain images with moving the ultrasound probe slantly to the body axis. Therefore, the plane of the ultrasonograph (scanning plane) is not perpendicular to the body axis of the subject, but inclines with respect to the body axis depending on degree of curve of body surface or organ surface, and direction in which the user puts the ultrasound probe on the surface. On the other hand, with an X-ray CT apparatus or MRI apparatus, an image of a section perpendicular to the direction of the body axis of the subject is obtained, and such imaging is repeated a plurality of times to obtain volume data.

Therefore, in order to carry out alignment of both the images by an automatic alignment method, it is necessary to rotate volume data obtained with an X-ray CT apparatus or MRI apparatus according to the inclination from the body axis in the ultrasonograph. General automatic alignment methods are methods of automatically extracting a characteristic shape included in the two images, and calculating moving magnitude through pattern matching or the like so that the characteristic shapes of the images coincide to each other. The inclination angle with respect to the body axis in the ultrasonograph is not a small angle, and differs depending on type of organ, direction along which the user desired to see it, or the like. Since resolutions of ultrasonograph and volume data obtained with an X-ray CT apparatus or MRI apparatus greatly differ, extracted shapes differ even if they are those for the same characteristic shape. In addition, the extracted shapes are three-dimensional shapes. For these reasons, the automatic alignment is difficult, and in order to carry out automatic alignment, huge amount of calculation is required. Therefore, such calculation requires much time to keep the abdominally incised subject and user waiting, and thus it has conventionally been difficult to actually carry out it.

According to the present invention, such a configuration as described below is employed in consideration that shape of surface of a specific organ is substantially the same although there is some individual difference, and the direction along which users desire to see an imaging part (part of internal organ) is also substantially the same for each imaging part. That is, volume data obtained with another medical imaging apparatus are first initially rotated by a rotation amount corresponding to a specific part of internal organ. Then, alignment of ultrasonograph and volume data obtained with another medical imaging apparatus is carried out by the automatic alignment method. This makes it possible to perform automatic alignment with sufficient accuracy in a short time. As the rotation amount of the initial rotation, a value determined beforehand for each imaging part (part of internal organ) may be used as in the embodiment 1, or it may be calculated for each imaging part as in the embodiment 2.

Embodiment 1

As for the configuration of the ultrasonic imaging apparatus of the present invention, the apparatus comprises, for example, an ultrasound probe 7, a position sensor 8, an image generator 107, and an image processing device 108, as shown in FIG. 1. The ultrasound probe 7 transmits ultrasonic waves to a subject 120, and receives ultrasonic waves reflected by the subject 120. The position sensor 8 is attached to the ultrasound probe 7. The image generator 107 generates an ultrasonograph from the signals received by the ultrasound probe 7, and generates first volume data from the ultrasonograph and positional information of the ultrasound probe 7 obtained from the position sensor 8. The image processing device 108 receives second volume data obtained by another external imaging apparatus for the subject 120, and processes them. For this processing, the image processing device 108 carries out alignment of the first volume data and the second volume data. The image processing device 108 receives a predetermined imaging part selected by a user from a plurality of imaging parts of the subject, obtains a rotation angle corresponding to the received imaging part on the basis of relation of a plurality of imaging parts and rotation angles defined beforehand, and initially rotates the second volume data by the obtained rotation angle. The image processing device 108 further carries out alignment of the initially rotated second volume data and the first volume data to enable automatic alignment with good accuracy in a short time.

<Configuration and Operation>

Hereafter, specific configuration of the ultrasonic imaging apparatus of the embodiment 1 will be further explained. As shown in FIG. 1 and mentioned above, the ultrasonic imaging apparatus of this embodiment comprises the ultrasound probe 7, position sensor 8, image generator 107, and image processing device 108, and further comprises a transmitter 102, a transmission and reception switch 101, a receptor 105, a position detection unit 6, a user interface 121, and a controller 106. Under control by the controller 106, the transmitter 102 generates transmission signals and sends them to each of a plurality of ultrasonic wave devices constituting the ultrasound probe 7. As a result, each of the plurality of the ultrasonic devices of the ultrasound probe 7 transmits ultrasonic waves toward the subject 120. The ultrasonic waves, for example, reflected by the subject 120 reach the plurality of the ultrasonic devices of the ultrasound probe 7 again, and are received thereby and converted into electric signals. The signals received by the ultrasonic devices are delayed by the receptor 105 for predetermined delaying amounts corresponding to the position of reception focus, and then added (phasing addition). This processing is repeated for a plurality of the reception focuses. The signals subjected to the phasing addition are sent to the image generator 107. The transmission and reception switch 101 selectively connects the transmitter 102 or receptor 105 to the ultrasound probe 7.

The position detection unit 6 detects the position of the ultrasound probe 7 from output of the position sensor 8. For example, a magnetic sensor unit can be used as the position detection unit 6. The position detection unit 6 forms a magnetic field space, the position sensor 8 detects the magnetic field, and coordinates from a position serving as a base point can be thereby detected.

The image generator 107 carries out processings such as arranging the phase-added signals received from the receptor 105 at corresponding positions to generate an ultrasonograph. The image generator 107 further receives positional information of the ultrasound probe 7 at that position from the position detection unit 6, and imparts positional information to the ultrasonograph. As a result, when a user moves the ultrasound probe 7 in a predetermined area, the image generator 107 generates an ultrasonograph imparted with the positional information of the ultrasound probe 7 at that position, and volume data of three-dimensional ultrasonograph (henceforth also referred to as ultrasonic volume data or first volume data) can be thereby generated.

The image processing device 108 receives volume data obtained for the subject 120 by another imaging apparatus (second volume data) via the user interface 121, and carries out alignment of the first volume data and the second volume data, and so forth. In the following explanation, the other imaging apparatus such as ultrasonic MRI apparatus, X-ray CT apparatus, and other ultrasonic diagnostic apparatuses is referred to as medical modality. In this embodiment, for example, an X-ray CT apparatus is used as the medical modality, and volume data of X-ray CT apparatus are referred to as CT volume data (second volume data).

Hereafter, configurations and operations of the image processing device 108 and the user interface 121 will be explained in detail.

Figure 2:
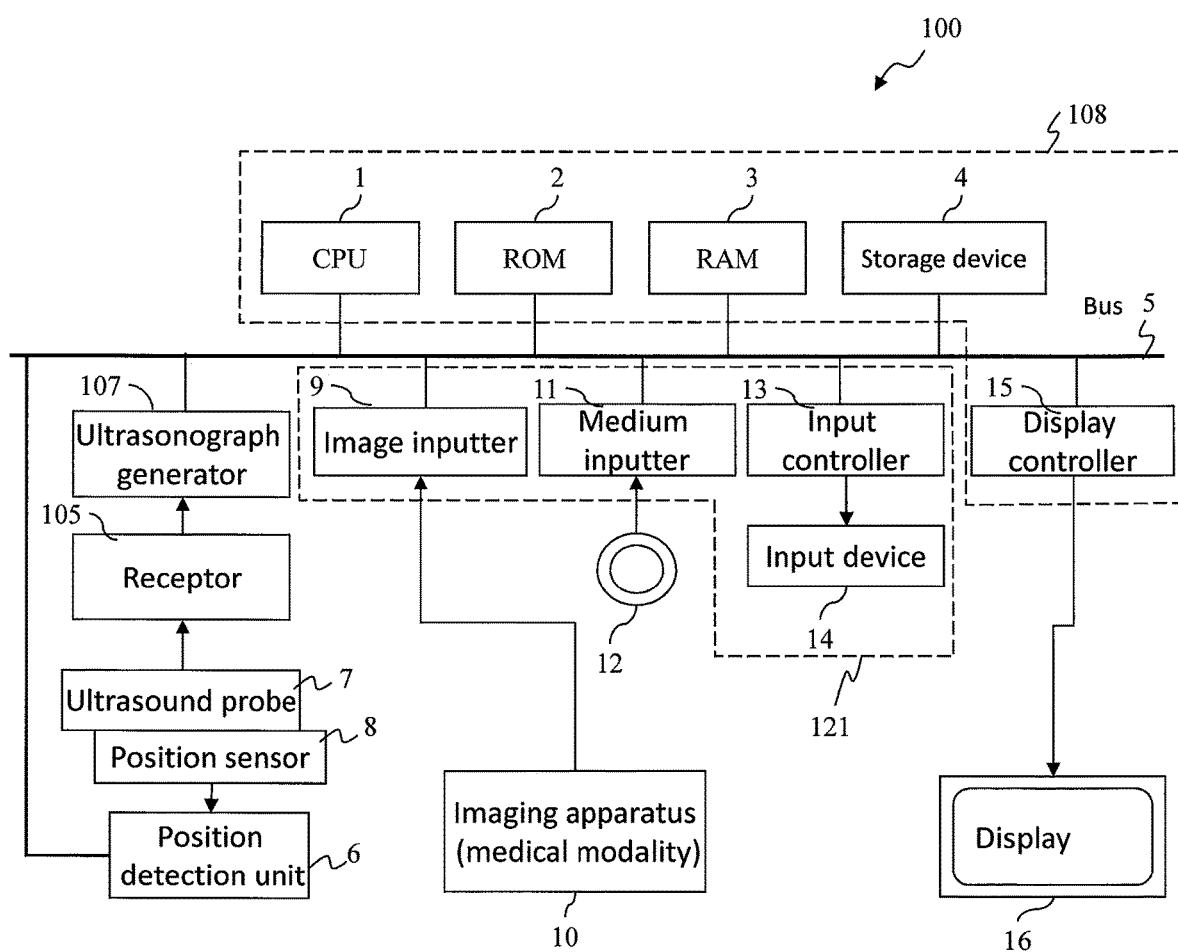
FIG. 2 A block diagram showing hardware configuration of the ultrasonic imaging apparatus of the embodiment 1.

FIG. 2 is a block diagram showing the hardware configurations of the image processing device 108 and the user interface 121. The hardware configurations shown in FIG. 2 are commonly used also in the other embodiments mentioned later.

The image processing device comprises and is constituted by CPU (processor) 1, ROM (non-volatile memory, read-only storage medium) 2, RAM (volatile memory, data-writable storage medium) 3, a memory 4, and a display controller 15. The user interface 121 comprises and is constituted by an image inputter 9, a medium inputter 11, an input controller 13, and an input device 14. These parts, and the ultrasonograph generator 6 and position detection unit 6 are connected with each other via a data bus 5. A display 16 is connected to the display controller 15.

A program and data required for realizing the operation of the image processing device 108 in the operation processing performed by CPU 1 are stored beforehand in at least one of ROM 2 and RAM 3. When CPU 1 executes the program stored beforehand in at least one of ROM 2 and RAM 3, various processings of the image processing device 108 are realized. The program executed by CPU 1 may also be stored in a storage medium (for example, optical disc) 12, and a medium inputter 11 (for example, optical disc drive) may read the program, and load it in RAM 3. The program may also be stored in a storage device 4, and loaded in RAM 3 from the storage device 4. The program may also be stored in ROM 2 beforehand.

The image inputter 9 is an interface for inputting CT volume data (second volume data) obtained with an X-ray CT apparatus (medical modality) 10. The storage device 4 is a magnetic storage device that stores the second volume data and so forth inputted via the image inputter 9. The storage device 4 may be provided with a non-volatile semiconductor storage medium (for example, flash memory). An external storage device connected via a network or the like may also be used.

The input device 14 is a device for receiving operations of a user, and may comprise, for example, a keyboard, trackball, navigational panel, foot switch, and so forth. The input controller 13 is an interface for receiving the input for the operations inputted by the user. The input for the operations received by the input controller 13 is processed by CPU 1.

The display controller 15 performs control so that, for example, image data obtained by processings in CPU 1 are displayed on the display 16. The display 16 displays an image under control by the display controller 15.

Figure 3:
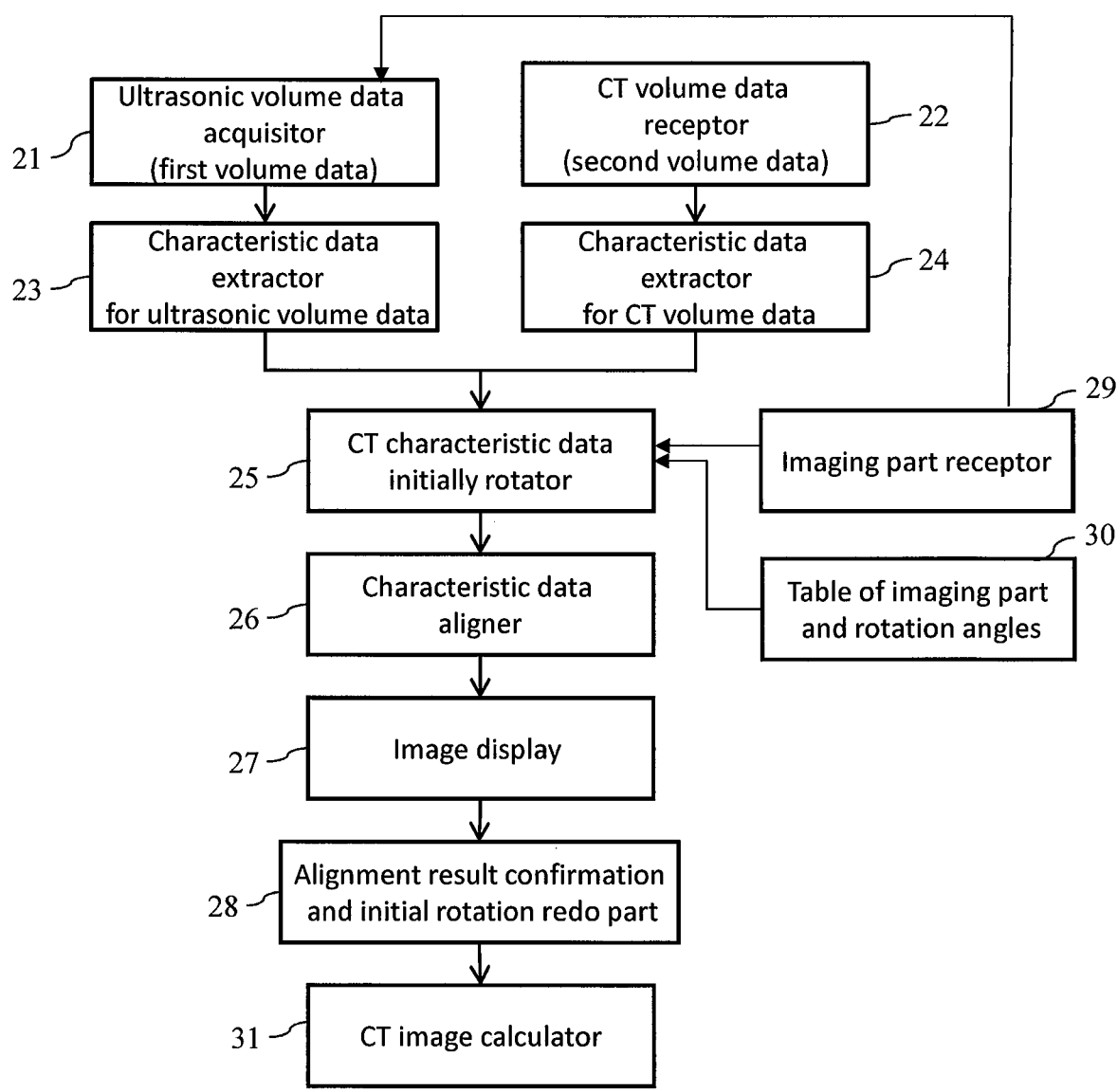
FIG. 3 A functional block diagram of the image processing device 108 of the ultrasonic imaging apparatus of the embodiment 1.

FIG. 3 is a functional block diagram showing the functions of the image processing device 108. As shown in FIG. 3, the image processing device 108 comprises an ultrasonic volume data (first volume data) acquisitor 21, a characteristic data extractor 23 for ultrasonic volume data, a CT volume data receptor 22, and a characteristic data extractor 24 for CT volume data. The image processing device 108 also comprises a CT characteristic data initially rotator 25 and a characteristic data aligner 26 as an aligner. It further comprises an image display 27, an alignment result confirmation and initial rotation redo part 28, and a CT image calculator 31.

Figure 4:
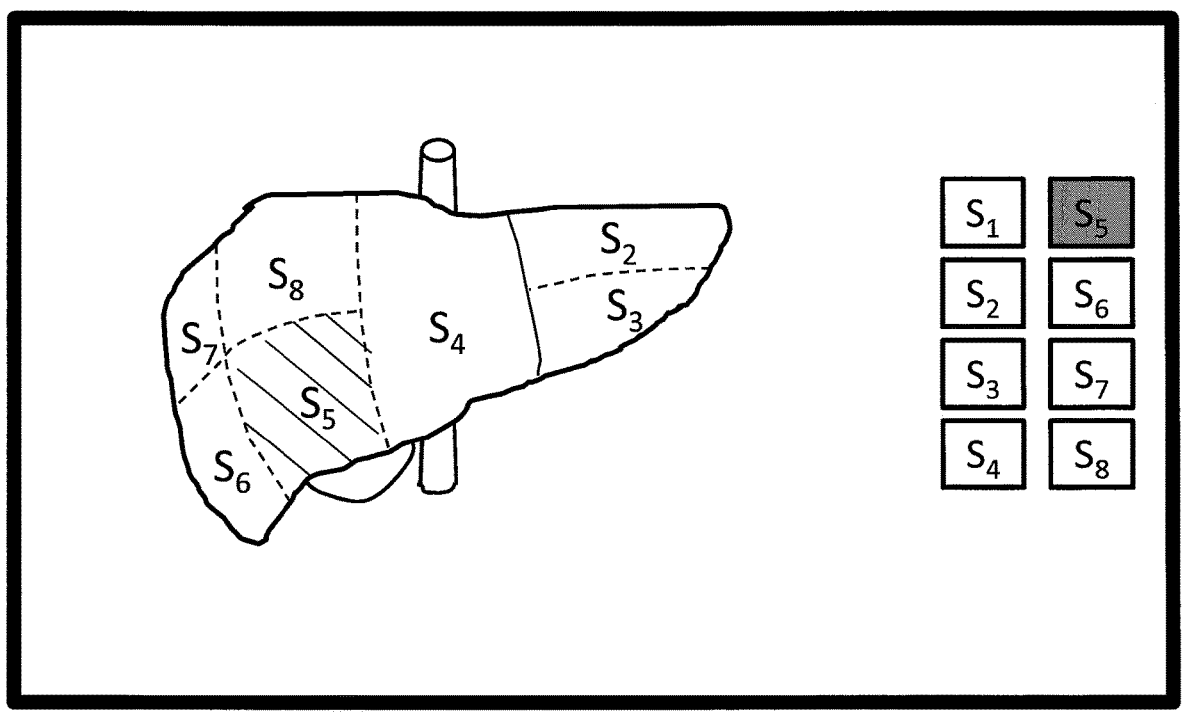
FIG. 4 An explanatory drawing showing an example of screen for receiving an imaging part (zone of internal organ) from a user according to the embodiment 1.
Figure 4:
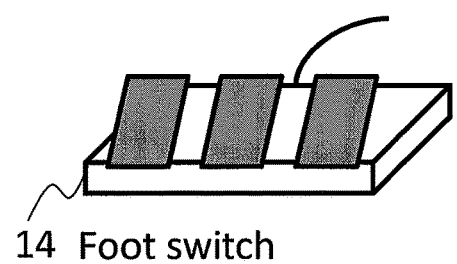

The image processing device 108 further comprises an imaging part receptor 29 and a table 30 showing relation between a plurality of imaging parts and rotation angles. As shown in FIG. 4, the receptor 29 is a functional block for displaying a screen on the display 16 for receiving zones S1 to S8 of an internal organ (liver) chosen from the input device 14 by a user, and receiving a zone selected from the zones S1 to S8 by the user via the input device 14. The zones S1 to S8 are set according to an anatomically known sectionalization method, and surface shapes and internal structures of the zones are also anatomically known. Therefore, the angles at which a user puts the ultrasound probe 7 on the organ are substantially fixed for the zones depending on the surface shapes and internal structures of the zones, thus the rotation angles for the ultrasonograph to be obtained and with respect to the body axis of the subject are calculated beforehand, and the table 30 showing the angles corresponding to the zones is prepared as shown in FIG. 5. The table 30 is stored beforehand in ROM 2, RAM 3, or the storage device 4. Distances for parallel translation of the zones are also shown in the table shown in FIG. 5. These are distances of parallel translation for the cases where parallel translation is also required besides rotation, when the CT image is coincided by rotation to the ultrasonograph obtained with the inclination. As for alignment by parallel translation, the alignment can be performed by a known alignment method with processing in the characteristic data aligner 26, and therefore the table 30 may not necessarily contain parallel translation distances. Since it is considered that the rotation angle should differ depending on sex and age of the subject, and whether the subject is abdominally incised or not, a plurality of kinds of different tables 30 may be prepared, and one of them may be chosen and used.

Hereafter, the processings performed by the image processing device 108 will be explained with reference to the flowchart shown in FIG. 6.

First, in the step S201, the CT volume data receptor 22 receives CT volume data from the imaging apparatus (X-ray CT apparatus) 10 via the image inputter 9.

In the step S202, the imaging part receptor 29 displays such an image for receiving specification of a zone of an internal organ as shown in FIG. 4 on the display 16, and receives specification of a zone of an internal organ (S1 to S8) made by a user through a touch on a touch panel of the screen, or an operation using the input device 14 such as foot switch.

In the step S203, the ultrasonic volume data acquisitor 21 displays an indication urging the user to put the ultrasound probe 7 on the zone of the internal organ and move it (perform scanning) on the display 16. When the user moves the ultrasound probe 7 in the zone of the internal organ, three-dimensional ultrasonic volume data are generated by the transmitter 102, the receptor 105, and the image generator 107. The ultrasonic volume data acquisitor 21 receives the ultrasonic volume data generated by the image generator 107. For example, if the user performs scanning with putting the ultrasound probe on the liver zone S5, data for the portal vein, which is a characteristic part of the liver, are included in the ultrasonic volume data.

Figure 7:
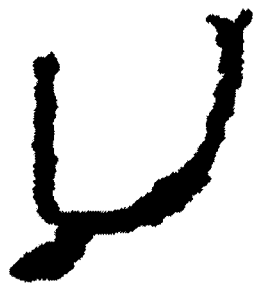
FIG. 7 Explanatory drawings showing examples of images of first characteristic data (ultrasonic blood vessel data) (FIG. 7A), second characteristic data (CT blood vessel data) (FIG. 7B), and initially rotated second characteristic data (CT blood vessel data) (FIG. 7C) according to the embodiment 1.
Figure 7:
Figure 7:

In the step S204, the characteristic data extractors 23 and 24 extract point group data of the characteristic parts such as blood vessel contained in the ultrasonic volume data and CT volume data, respectively. The extracted blood vessel data are three-dimensional coordinate data of voxels in segmented vascular regions. Blood vessel data extracted from the ultrasonic volume data are shown in FIG. 7A, and blood vessel data extracted from the CT volume data are shown in FIG. 7B. Although FIGS. 7A and 7B show blood vessel data of the corresponding internal organ zone, resolutions of the ultrasonic volume data and CT device volume data greatly differ from each other, and in addition, the imaging directions and views thereof are also greatly differ from each other. Therefore, the shapes of the blood vessel data of the both also greatly differ from each other.

In the step S205, the CT characteristic data initially rotator 25 rotates the CT blood vessel data extracted in the step S204 according to the internal organ zone specified in the step S202. That is, the CT characteristic data initially rotator 25 refers to the table 30 of the internal organ zones and rotation angles shown in FIG. 5, reads the rotation angle corresponding to the internal organ zone specified in the step S202, and rotates the CT blood vessel data by the read rotation angle (initial rotation). When parallel translation distances are included in the table 30, it reads the parallel translation distance corresponding to the internal organ zone, and carries out parallel translation of the CT blood vessel data by that distance. The CT blood vessel data are thereby geometrically converted so that they are rotated by the angle corresponding to the inclination of the ultrasonograph specific to the internal organ zone, and therefore the initial positions of the ultrasonic blood vessel data and the CT blood vessel data are approximately coincided to each other. FIG. 7C shows the rotated CT blood vessel data. FIG. 7C shows that the direction of the rotated CT blood vessel data approximately corresponds to the direction of ultrasonic blood vessel data, and they show shapes that can be superimposed.

Then, in the step S206, the characteristic data aligner 26 performs alignment of the point groups of the ultrasonic blood vessel data and the rotated CT blood vessel data. Since the initial positions of the blood vessel data have already been approximately coincided in the step S205, alignment of the both can be performed by a known automatic alignment method. As such a known automatic alignment method, the known ICP (Iterative Closest Point) method can be used. By the ICP method, a point group of CT blood vessel data is geometrically converted (parallel translation and rotation), the distance from the corresponding point in the point group of the ultrasonic blood vessel data is obtained, and the calculation is repetitively performed so that the distance is minimized. The alignment of the both can be thereby carried out.

Figure 8:
FIG. 8 An explanatory drawing showing an example of image that superimposingly displays the aligned first characteristic data and second characteristic data according to the embodiment 1.

In the step S207, the image display 27 changes color of one of the aligned CT blood vessel data and ultrasonic blood vessel data after to generate a transparently superimposed image, and displays it on the display 16. As shown in FIG. 8, for example, there is displayed an image with which it can be confirmed that the aligned CT blood vessel data and ultrasonic blood vessel data can overlap with each other. The image display 27 may also apply the result of the alignment to the CT volume data, and display them so that they overlap with the ultrasonic volume data. The Image display 27 can also generate and display an image in which the aligned CT blood vessel data are transparently superimposed on the aligned CT volume data in a different color, and the ultrasonic blood vessel data are transparently superimposed on the ultrasonic volume data in a different color.

In a state that the image shown in FIG. 8 is displayed, the alignment result confirmation and initial rotation redo part 28 displays an indication inquiring whether the user judges that the alignment has been successfully performed or not on the display 16, and receives judgment of the user via the input device 14. When the user inputs a judgment that the alignment has been successfully performed via the input device 14, the alignment processing is ended, and in the step S210, the alignment result confirmation and initial rotation redo part 28 performs the rotation and parallel translation performed for the CT blood vessel data in the steps S205 and S206 for the whole CT volume data to generate aligned CT volume data.

On the other hand, when the user judges that the alignment has been unsuccessful, the process advances to the steps S208 and S209, and the alignment result confirmation and initial rotation redo part 28 redoes the initial rotation by another method. That is, in the steps S208 and S209, it obtains the rotation angle for the initial rotation of the CT volume data by calculation without using the rotation angles of the table 30.

Figure 9:
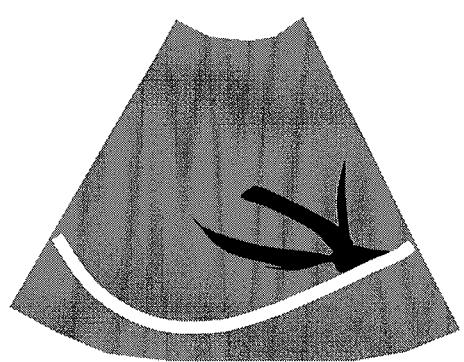
FIG. 9 Explanatory drawings showing examples of images of first characteristic section extracted from ultrasonic volume data (FIG. 9A), and second characteristic section extracted from CT volume data (FIG. 9B) according to the embodiment 1.
Figure 9:
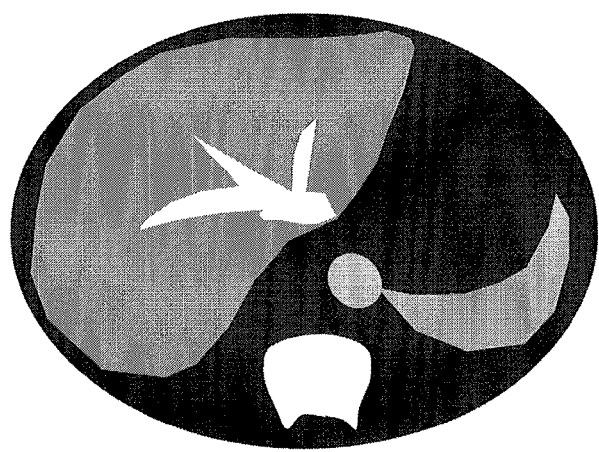

First, in the step S208, sections including a characteristic part defined beforehand for each internal organ zone are extracted from the ultrasonic volume data and the CT volume data not initially rotated in the step S205, respectively. For example, such images of a characteristic section including the inferior vena cava of the liver as shown in FIG. 9 are extracted and generated from ultrasonic volume data and CT volume data, respectively. FIG. 9A shows an example of sectional image of the inferior vena cava extracted from ultrasonic volume data. FIG. 9B shows an example of sectional image of the inferior vena cava extracted from CT volume data. As the method of searching for and extracting characteristic section, for example, the AdaBoost method, which is a known method of machine learning, can be used.

Then, in the step S209, the rotation angle by which the CT blood vessel data should be rotated is calculated by using the positional information of the two extracted images of the characteristic section so that the images should coincide to each other. The CT blood vessel data are rotated by the calculated rotation angle (initial rotation).

The process returns to the step S206, and alignment of the point groups of the ultrasonic blood vessel data and the rotated CT blood vessel data is performed. Until it is judged in the step S207 that the alignment is successfully performed, the steps S206, S207 S208, and S209 are repeatedly performed. If it is judged by the user that the alignment is successfully performed, the process advances to the step S210, the rotation and parallel translation performed for the CT blood vessel data in the steps S209 and S206 are performed for the whole CT volume data to generate aligned CT volume data.

By the procedures explained above, CT volume data aligned so that they coincide to the ultrasonic volume data are generated.

Figure 10:
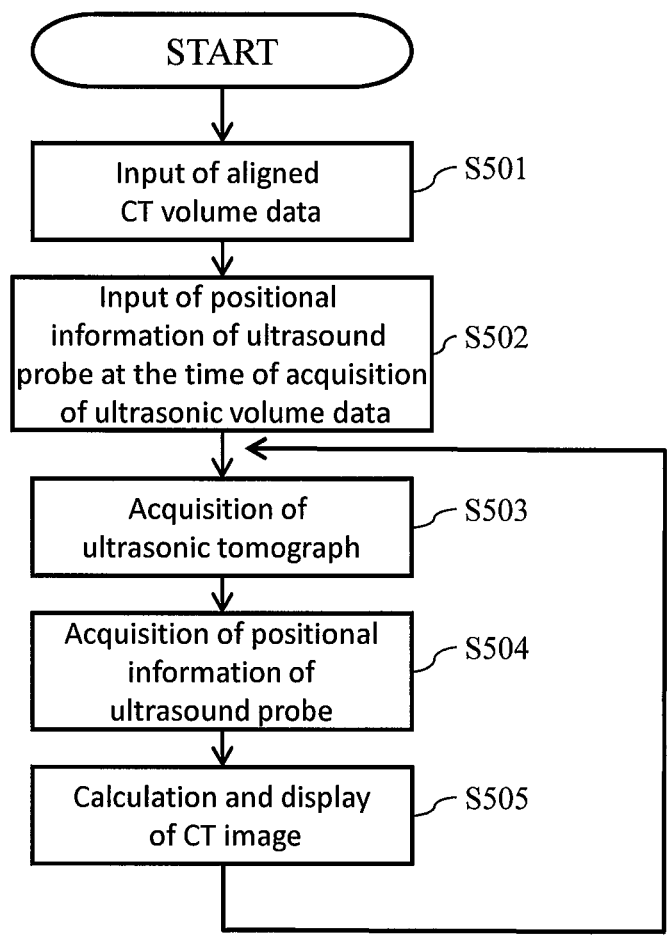
FIG. 10 A flowchart showing the processing for calculating CT image corresponding to ultrasonograph according to the embodiment 1.

Then, the CT image calculator 31 performs the process of the flowchart shown in FIG. 10 to generate a CT image of a section corresponding to the ultrasonograph generated by the ultrasound probe 7 at the current position, and display it with the ultrasonograph side by side.

Figure 6:
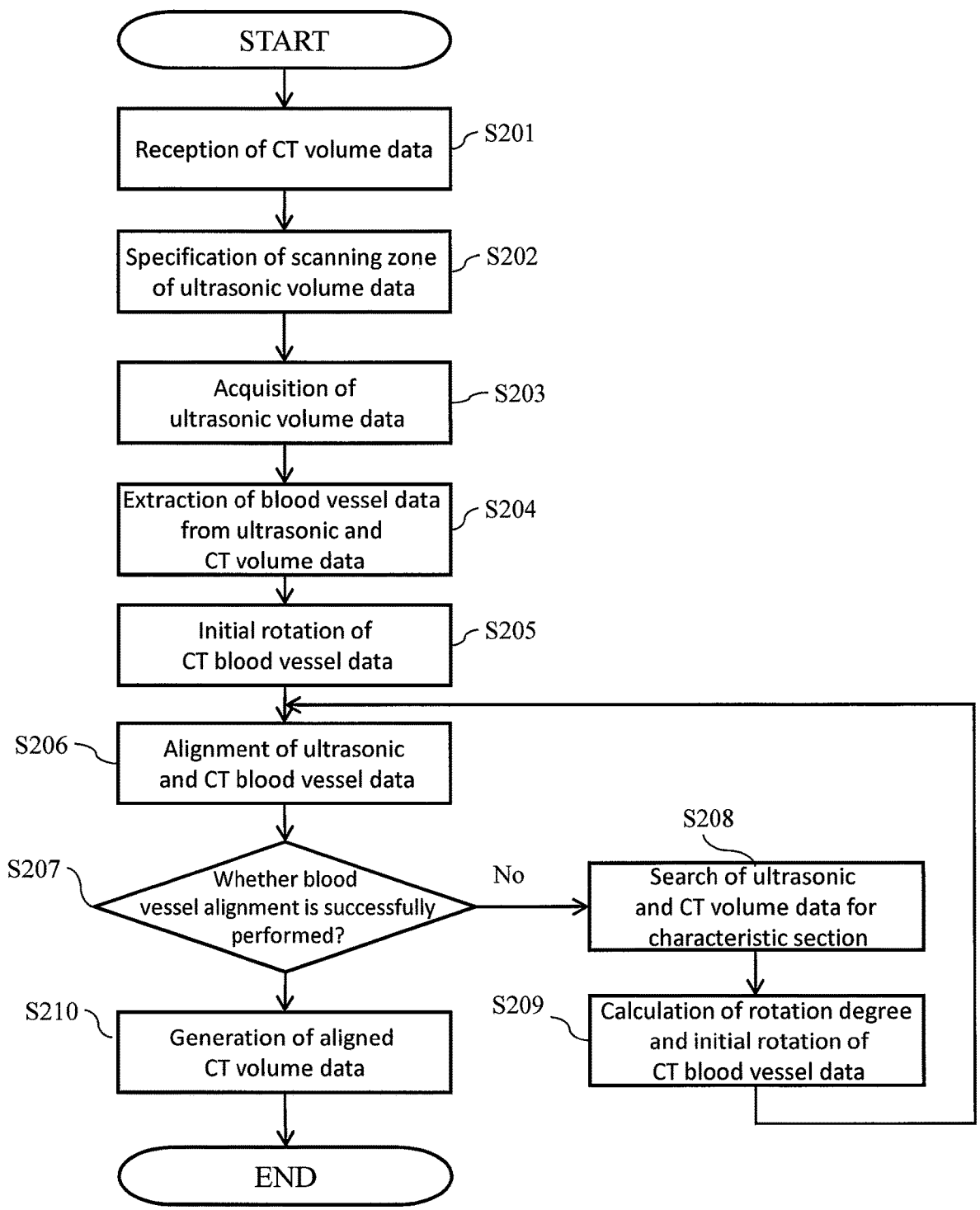
FIG. 6 A flowchart showing the alignment processing of the ultrasonic imaging apparatus according to the embodiment 1.

In the step S501 shown in FIG. 10, the CT image calculator 31 receives the aligned CT volume data generated in the step S210 shown in FIG. 6.

In the step S502, the positional information of the ultrasound probe 7 at the time of the acquisition of the ultrasonic volume data is received from the image generator 107. Then, when the user put the ultrasound probe 7 on the objective internal organ at a desired position, the image generator 107 is allowed to generate an ultrasonograph (step S503). At the same time, positional information of the ultrasound probe 7 is obtained from the position detection unit 6 (step S504).

The CT image calculator calculates positional relationship of the positional information of the ultrasound probe 7 at the time of the acquisition of the ultrasonic volume data obtained in the step S502, and the current positional information of the ultrasound probe 7 obtained in the step S504, and cuts out (calculates) a CT image of a section corresponding to the ultrasonograph generated in the step S503 from the aligned CT volume data received in the step S501 on the basis of the calculated positional relationship (step S505). By displaying the ultrasonograph obtained in the step S503, and the CT image obtained in the step S505 side by side, an ultrasonograph obtained with the ultrasound probe 7 and a CT sectional image of the same position can be generated and displayed in real time.

As explained above, according to this embodiment, CT volume data aligned so that they coincide to ultrasonic volume data can be generated. Since this alignment can be automatically carried out in a short time without calling on a user to perform complicated alignment processing, its burdens imposed on user and subject are small. Further, since the alignment is performed for three-dimensional data, i.e., ultrasonic volume data and CT volume data, accuracy of the alignment is high. Therefore, it becomes possible to display a CT image of high resolution or the like on an ultrasonograph of a narrow field including many noises so that the CT image highly precisely coincides to the ultrasonograph in real time, and therefore it becomes possible for a user to recognize even a small tumor or the like in the ultrasonograph.

According to this embodiment, the alignment processing of ultrasonic volume data and CT volume data is performed by extracting data of characteristic part (blood vessel), therefore the alignment can be carried out with blood vessel data of a smaller data amount compared with volume data, and thus calculation amount can be reduced. Accordingly, the alignment can be performed at high speed.

Although the embodiment 1 has been explained for the configuration that the image processing device 108 is provided in the inside of the ultrasonic imaging apparatus 100, it is also possible to provide the image processing device 108 shown in FIGS. 1 and 2 as an apparatus separate from the ultrasonic imaging apparatus 100. In such a case, the image processing device 108 and the ultrasonic imaging apparatus 100 are connected via a signal wire or network. For example, the following configuration is employed. The image processing device 108 is implemented in an image processing device such as common computer or workstation, and connected with the ultrasonic imaging apparatus 100 via a network. The image processing device 108 receives ultrasonic volume data and CT volume data to be aligned from a client terminal via a network, and performs the alignment processing. The aligned CT volume data are transmitted to the ultrasonic imaging apparatus as the client terminal. It is thereby made unnecessary that the image processing device 108 that requires comparatively large operation amount is carried on the ultrasonic imaging apparatus 100. The ultrasonic imaging apparatus 100 can perform the alignment processing by using operation ability of the image processing device 108 connected via a network. Therefore, there can be provided the ultrasonic imaging apparatus 100 that is small and simple, but can display an ultrasonograph and a CT image of the same section on real time.

Embodiment 2

In the embodiment 1, CT volume data are initially rotated by a rotation angle obtained beforehand for each zone of internal organ. However, the present invention is not limited to such a configuration, and the angle for the initial rotation can also be obtained by calculation. This configuration will be explained as the embodiment 2. In the explanation of the embodiment 2, the same configurations and processings as those of the embodiment 1 are indicated with the same numerals, and explanations thereof are omitted.

Figure 11:
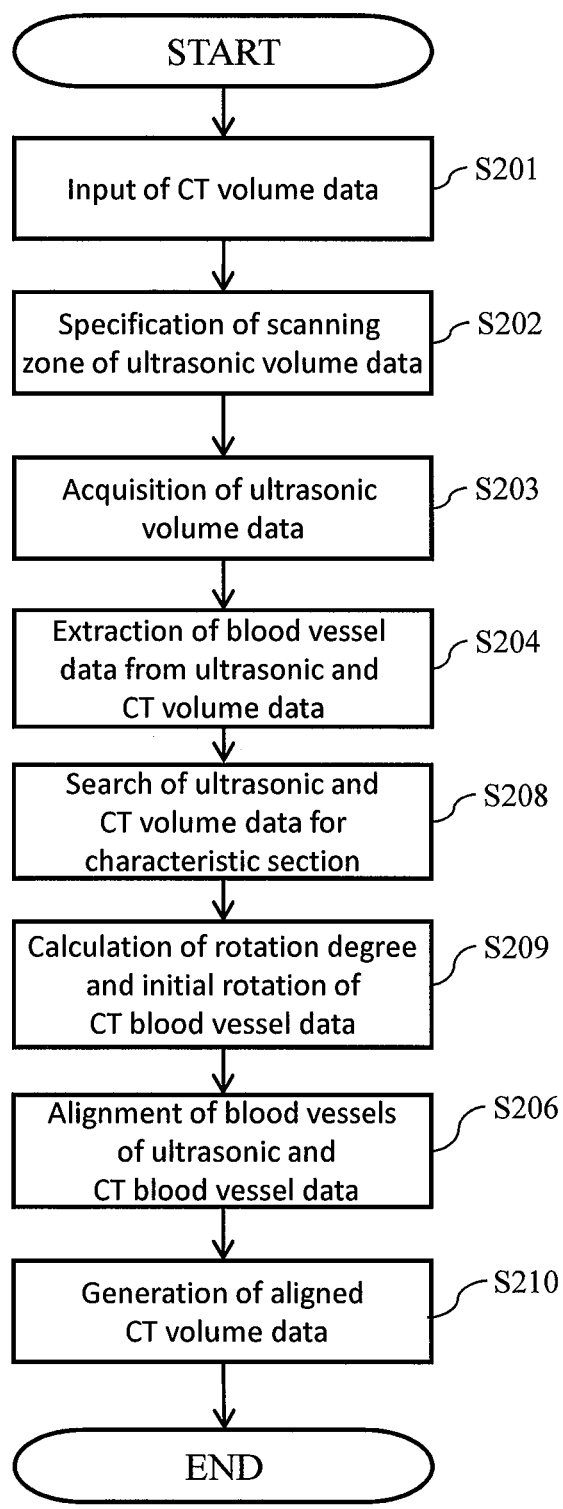
FIG. 11 A flowchart showing the alignment processing carried out by the ultrasonic imaging apparatus according to the embodiment 2.

The ultrasonic imaging apparatus of the embodiment 2 does not comprises the table 30 shown in FIG. 5 in which a rotation angle is matched with each imaging part. As shown in the flowchart of FIG. 11, in the steps S201 to S204, the image processing device 108 extracts ultrasonic blood vessel data and CT blood vessel data in the same manner as that of the embodiment 1. Then, the angle for the initial rotation of the CT blood vessel data is obtained by calculation through the steps S208 and S209 of the embodiment 1, and the CT blood vessel data are initially rotates by the obtained angle.

Specifically, the process advances to the step S208 after the step S204, and sections including a predetermined characteristic section included in the zone of internal organ specified in the step S202 are extracted from the ultrasonic volume data and the CT volume data not initially rotated, respectively. For example, images of such a characteristic section including the inferior vena cava of the liver as shown in FIGS. 9A and 9B are extracted from ultrasonic volume data and CT volume data, respectively. As the method of searching for and extracting characteristic section, for example, the AdaBoost method, which is a known method of machine learning, can be used.

Then, in the step S209, the rotation angle by which the CT blood vessel data should be rotated is calculated by using the positional information of the two extracted images of the characteristic section so that the images should coincide to each other. The CT blood vessel data are rotated by the calculated rotation angle (initial rotation).

Alignment is performed so that the initially rotated CT blood vessel data should coincide to the ultrasonic blood vessel data (step S206). Then, in the step S210, the rotation and parallel translation performed for the CT blood vessel data in the steps S209 and S206 are performed for the whole CT volume data to generate aligned CT volume data.

With the configuration of the embodiment 2, the initial rotation angle can be obtained by calculation, and therefore the embodiment 2 has an advantage that the initial rotation can be performed with an initial rotation angle matching with actual ultrasonic volume data and CT volume data. Further, since automatic alignment is performed after the initial rotation, the same effect as that of the embodiment 1 can be obtained.

Embodiment 3

The embodiment 3 will be explained below.

SUMMARY

In the embodiment 3, alignment accuracy is improved by further performing rigid body alignment for the ultrasonic volume data subjected to the alignment according to the embodiment 1 or 2, and aligned CT volume data.
<Configuration and Operation>

Figure 12:
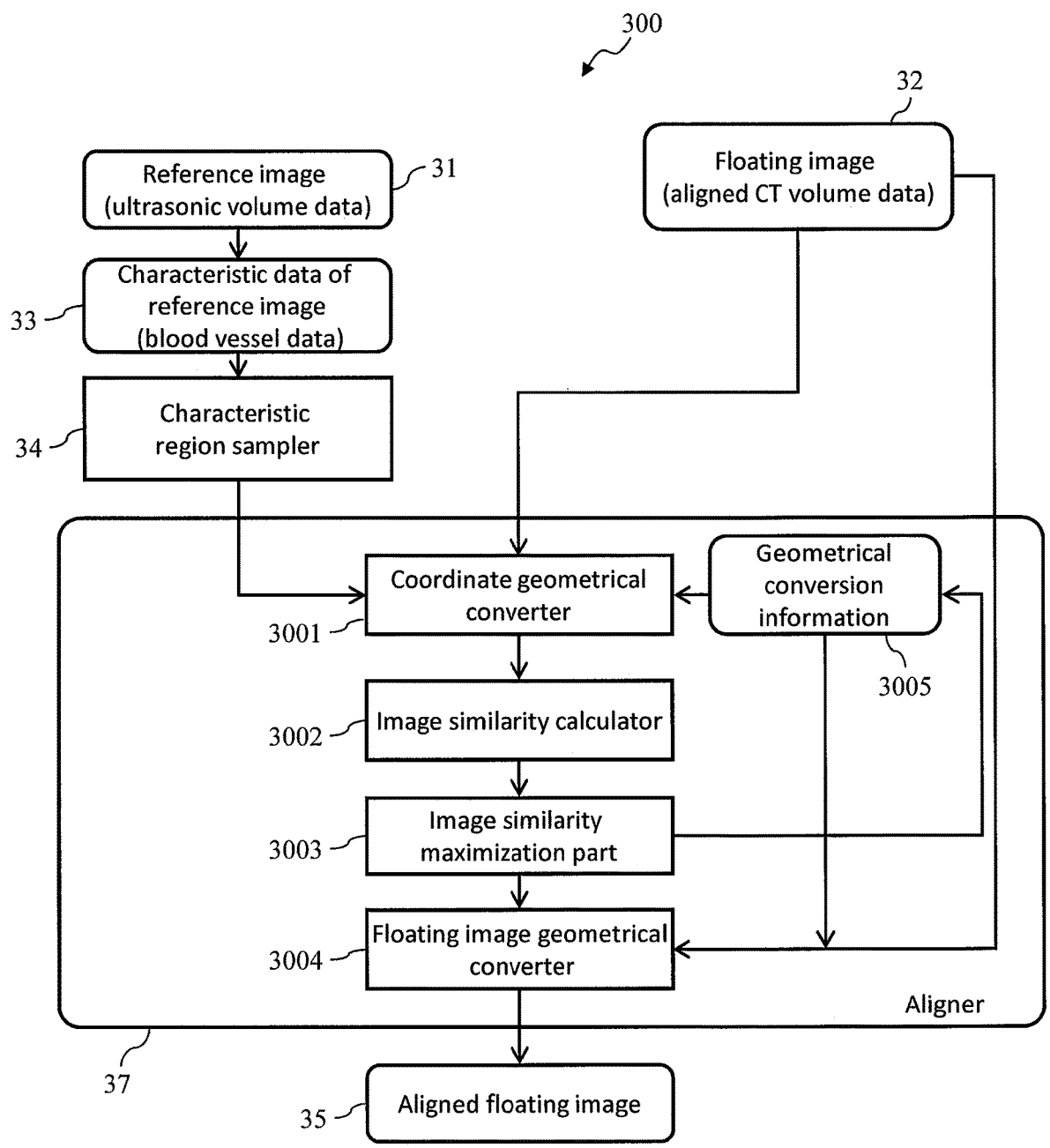
FIG. 12 A functional block diagram of the image-based rigid body alignment processor 300 according to the embodiment 3.

The ultrasonic imaging apparatus of the embodiment 3 further comprises, in addition to the functional blocks shown in FIG. 3, an image-based rigid body aligner 300 shown in FIG. 12 in the image processing device 108. The image-based rigid body aligner 300 is a device for performing alignment of the aligned CT volume data obtained in the step S210 of the embodiment 1 shown in FIG. 6 or the step S210 of the embodiment 2 shown in FIG. 6 as a floating image 32, and ultrasonic volume data as a reference image 31.

The image-based rigid body aligner 300 comprises a characteristic region sampler 34 and an aligner 37.

Figure 13:
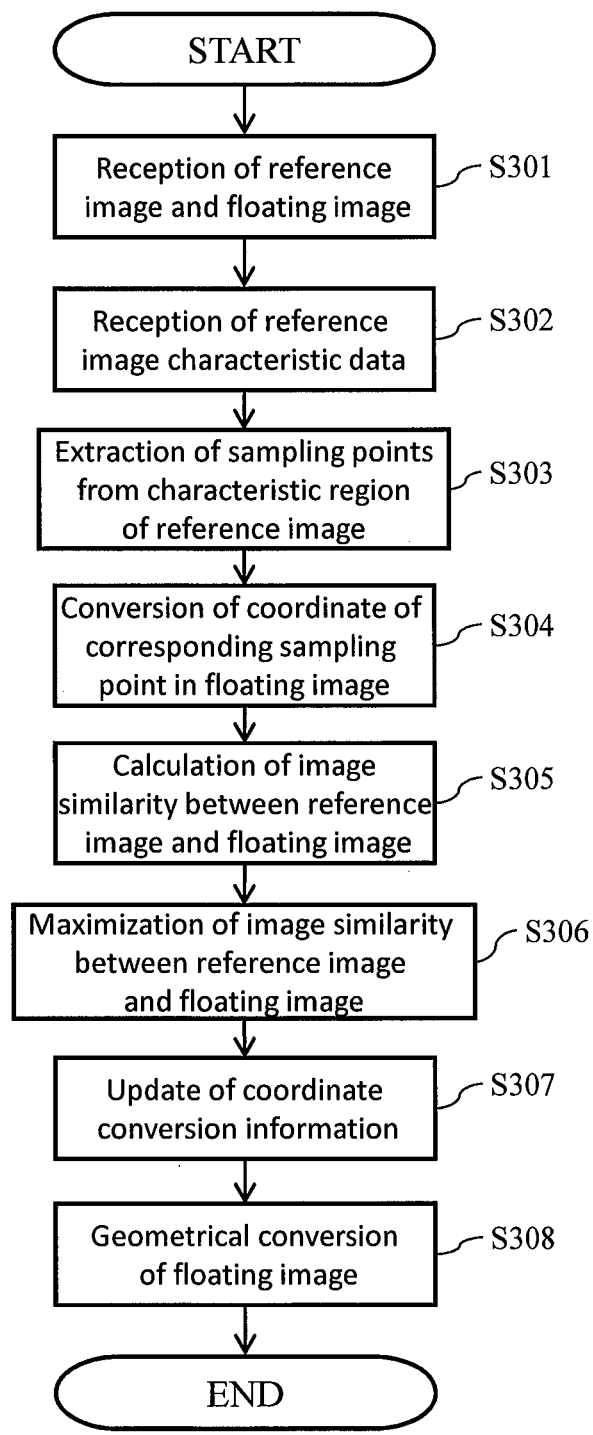
FIG. 13 A flowchart of the image-based rigid body alignment processing according to the embodiment 3.

FIG. 13 shows a flowchart for explaining the while operation of the rigid body aligner 300. The steps shown in FIG. 13 will be explained below.

The ultrasonic volume data as the reference image 31, and the aligned CT volume data obtained in the step S210 of the embodiment 1 or 2 as the floating image are inputted into the rigid body aligner 300 (S301). The characteristic region sampler 44 receives characteristic data of the ultrasonic volume data (ultrasonic blood vessel data) 33 extracted in the step S204 of the embodiments 1 and 2 (S302). The characteristic region sampler 44 extracts image sampling points at the coordinates of the reference image 31 and the characteristic data of the reference image 31, and outputs them to the aligner 37 (S303). These image sampling points are used for calculating image similarity of the reference image 31 and the floating image 32 in the aligner 37.

As for the extraction of the image sampling points, although all the pixels of the reference image 31 as the object of the alignment processing and the imaging region of the characteristic data of the reference image 31 may be extracted as the sampling points, only the pixels at nodes of grid placed on the images may be used as the sampling points in order to improve the speed of the alignment processing. A predetermined number of coordinates may be randomly chosen from coordinates of a region as the object of the sampling, for example, the characteristic data of the reference image 31, and luminosity values at the obtained coordinates may be used as luminosity values of the sampling points.

The aligner 37 comprises geometrical conversion information 3005, a coordinate geometrical converter 3001, an image similarity calculator 3002, an image similarity maximization part 3003, and a floating image geometrical converter 3004.

The geometrical conversion information 3005 is information representing the result of the alignment of the ultrasonic blood vessel data and the CT blood vessel data. That is, as the initial value for the image-based rigid body alignment performed in the aligner 37, the result of the alignment of the ultrasonic blood vessel data and the CT blood vessel data is used.

The coordinate geometrical converter 3001 geometrically converts the coordinates of the sampling points extracted from the reference image 31 to coordinates of corresponding points in the floating image 32 (S304). The image similarity calculator 3002 obtains luminosity data at the sampling points of the reference image 31, and luminosity data at the corresponding sampling points of the floating image 32. The image similarity calculator 3002 applies a predetermined evaluation function to the luminosity data at these sampling points to calculate image similarity between the reference image 31 and the floating image 32 (S305). As the image similarity, a known mutual information amount can be used.

The image similarity maximization part 3003 obtains the image similarity between the reference image 31 and the floating image 32 calculated by the image similarity calculator 3002. In this part, convergence calculation is carried out in order to obtain geometrical conversion information that provides the maximum (or local maximum) of the image similarity between the reference image 31 and the floating image 32 (S306). When the image similarity has not converged in the step S306, the image similarity maximization part 3003 updates the geometrical conversion information 3005 in order to obtain a higher image similarity (S307). Then, the steps S304 to S306 are performed again by using the updated geometrical conversion information 3005.

On the other hand, when the image similarity has converged in the step S306, the aligner 37 geometrically converts the floating image 32 by using the obtained geometrical conversion information 3005 to generate an aligned floating image 36 (S308). By performing the above processings, the processings of the aligner 37 are completed.

As explained above, in this embodiment 3, the rigid body aligner 300 carries out the image-based rigid body alignment of the reference image 31 (ultrasonic volume data) and the floating image 32 (CT volume data). The rigid body aligner 300 extracts sampling points from the reference image 31 by using the characteristic data 33 of the reference image. The rigid body aligner 300 calculates coordinates corresponding to the sampling points of the extracted reference image 31 in the floating image 32 by using the result of the alignment of the ultrasonic blood vessel data and the CT blood vessel data as initial value for the geometrical conversion. The rigid body aligner 300 calculates image similarity by using the sampling points of the reference image 31 and the corresponding sampling points of the floating image 32. Updating calculation of the geometrical conversion information of the floating image 32 is carried out so that the calculated image similarity should be maximized. As a result, an appropriate initial value for the geometrical conversion can be used, the image similarity can be calculated with good accuracy for an objective internal organ, and therefore stable and highly precise alignment processing can be realized.

As described above, alignment accuracy can be improved by further performing rigid body alignment for the ultrasonic volume data and CT volume data aligned according to the embodiment 1 or 2. Therefore, if a CT image is obtained by performing the process of the flowchart shown in FIG. 10 using the ultrasonic volume data and the CT volume data aligned according to this embodiment 3, real time ultrasonograph and CT image can be further highly precisely coincided to each other. Therefore, highly precise matching is possible between the both images, and small tumors and so forth can be confirmed with higher precision.

Embodiment 4

The embodiment 4 will be explained below.

SUMMARY

In the embodiment 4, alignment accuracy is improved by further performing non-rigid body alignment for the ultrasonic volume data aligned according to the embodiment 1 or 2, and the aligned CT volume data. That is, the image processing device 108 comprises, in addition to the functional blocks shown in FIG. 3, an image-based non-rigid body aligner 400 shown in FIG. 14 in the inside. The image-based non-rigid body aligner 400 is a device for performing alignment of the aligned CT volume data obtained in the step S210 of the embodiment 1 shown in FIG. 6 or the step S210 of the embodiment 2 shown in FIG. 11 as a floating image 42, and ultrasonic volume data as a reference image 41.

The image-based non-rigid body aligner 400 transforms the floating image 42 by using the aligned CT volume data as the floating image 42, and the ultrasonic volume data as the reference image 41. In order to transform the floating image 42, a control grid is placed on the floating image 42, and by moving control points in this control grid, the floating image is transformed. Image similarity is obtained between the transformed floating image and the reference image, and optimization calculation is performed on the basis of the obtained image similarity to obtain moving magnitudes of the control points in the control grid (transformation magnitude). In this calculation, the moving magnitude of a pixel between the control points in the control grid is calculated by interpolation of moving magnitudes of control points provided around that pixel. By using the obtained moving magnitude of each pixel, coordinate conversion of the floating image is performed, and such alignment that the image is locally changed is carried out. Deformation of internal organ and so forth can be thereby corrected, and accuracy and robustness of the alignment can be further improved.

Before the transformation of the floating image 42, the control points in the control grid are geometrically converted as an initial value for the non-rigid body alignment in order to arrange the control points at more exact positions. For this geometrical conversion of the control points, the result of the alignment of the point group of the ultrasonic blood vessel data and the point group of CT blood vessel data of the embodiment 1 or 2 may be used. Alternatively, the result of the rigid body alignment of the ultrasonic volume data and CT volume data of the embodiment 3 may also be used.

The configurations of the alignment of the point group of ultrasonic blood vessel data and the point group of CT blood vessel data, and the rigid body alignment of ultrasonic volume data and CT volume data are the same as those of Examples 1 or 2, and therefore differences are mainly explained below.

<Configuration and Operation>

Figure 14:
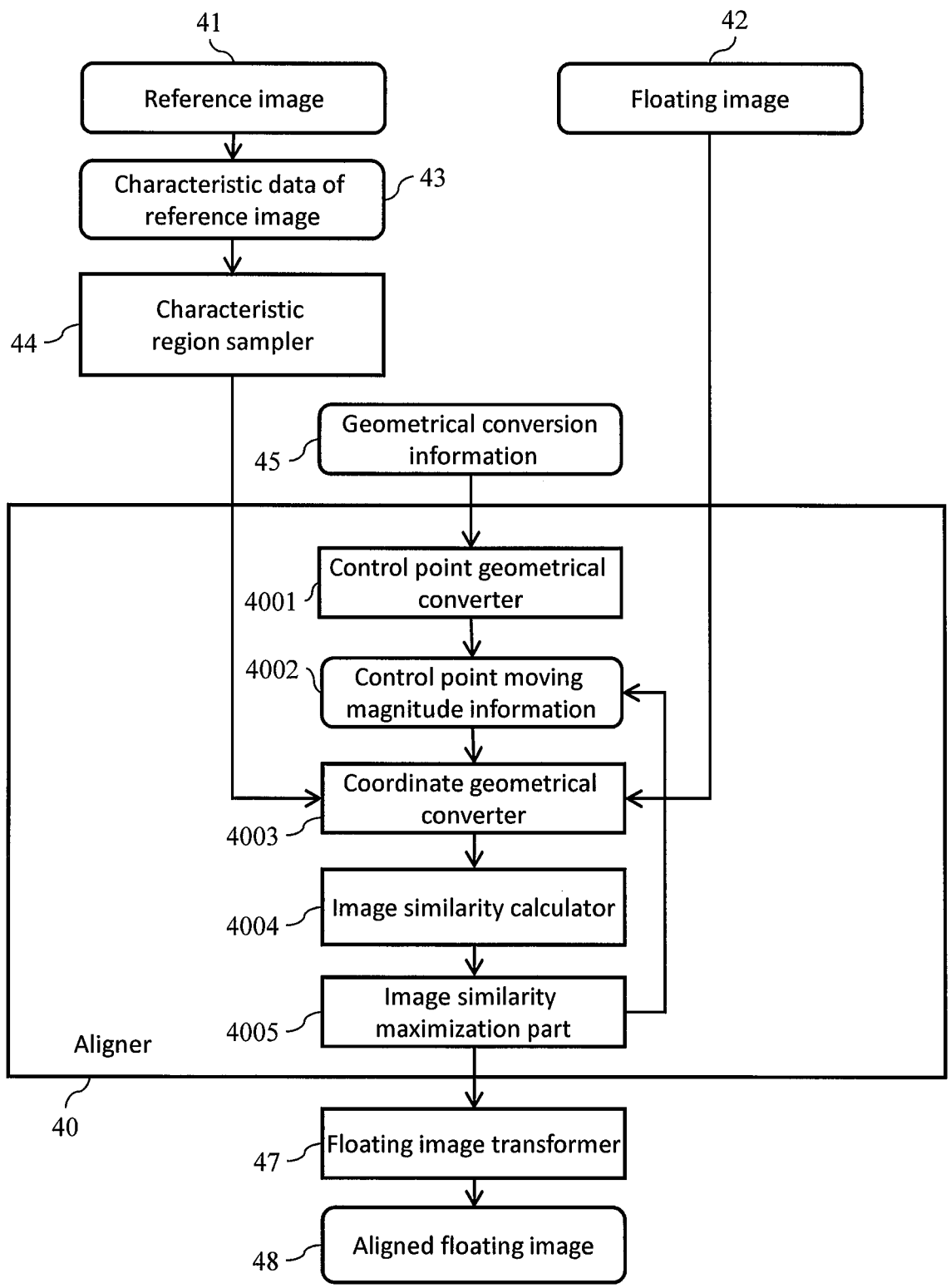
FIG. 14 A functional block diagram of the image-based non-rigid body alignment processor 400 according to the embodiment 4.

FIG. 14 shows a functional block diagram of the image-based non-rigid body aligner 400 of the ultrasonic imaging apparatus according to this embodiment. The image-based non-rigid body aligner 400 is a device for transforming the floating image 42 according to the reference image 41 to generate an aligned floating image 48, and comprises a characteristic region sampler 44, a control point geometrical converter 46, an aligner 40, and a floating image transformer 47.

The reference image 41, the floating image 42, and characteristic data 43 of the reference image are the same as the reference image 31, the floating image 32, and the characteristic data 33 of the reference image of the embodiment 3, respectively. The characteristic region sampler 44 receives the reference image 41 and the characteristic data 43 of the reference image, performs the same processings as those performed by the characteristic region sampler 34 of the embodiment 3, and outputs the obtained sampling points of the reference image 41 to the aligner 40.

The geometrical conversion information 45 is information outputted to the aligner 40 as initial value for the non-rigid body alignment. As the geometrical conversion information 45, the result of the alignment of the ultrasonic blood vessel data and the CT blood vessel data may be used, or the result of the rigid body alignment of the ultrasonic volume data and the CT volume data may be used.

The aligner 40 comprises a control point geometrical converter 4001, a coordinate geometrical converter 4003, an image similarity calculator 4004, and an image similarity maximization part 4005.

Figure 15:
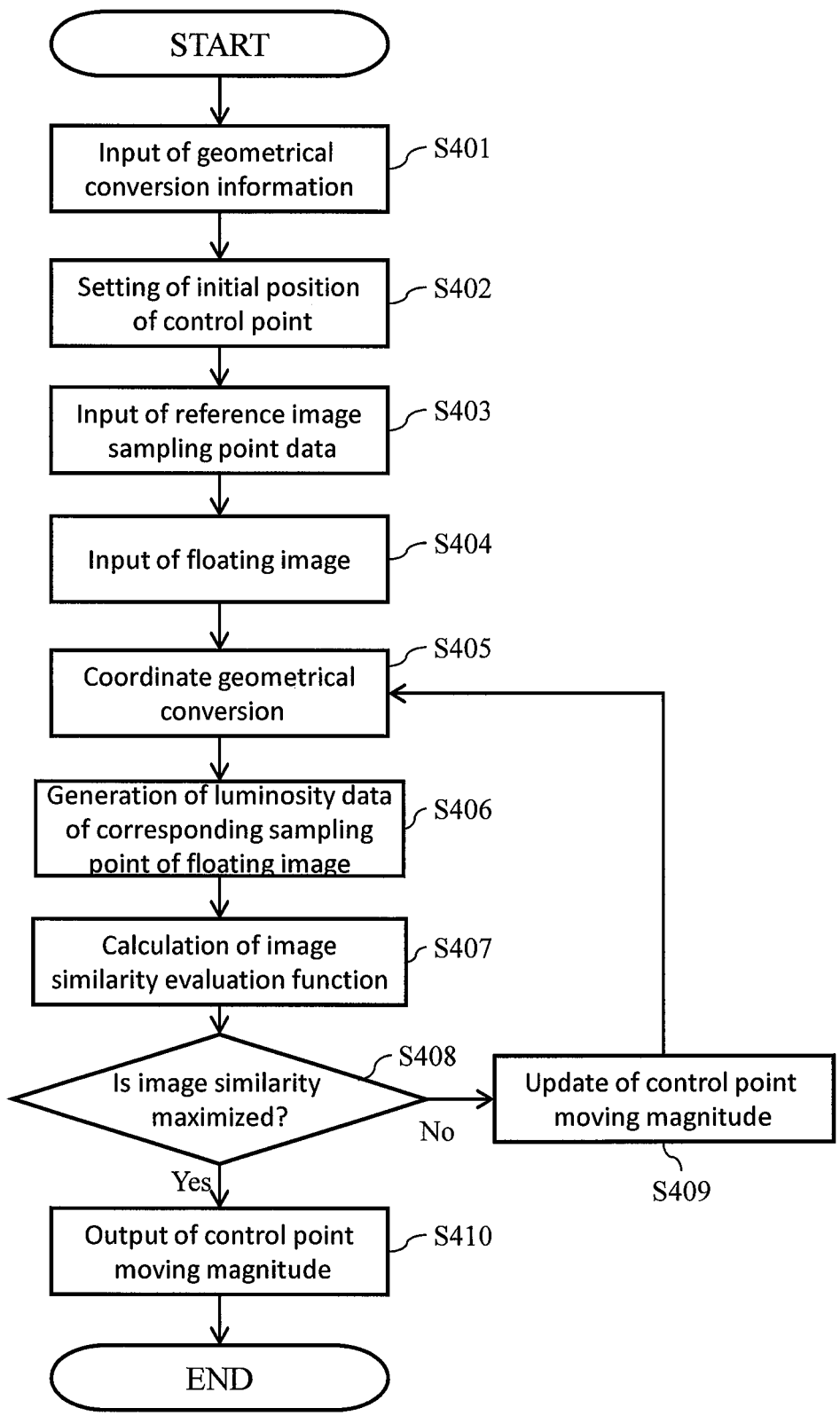
FIG. 15 A flowchart of the image-based non-rigid body alignment processing according to the embodiment 4.

FIG. 15 is a flowchart for explaining the whole operation of the aligner 40. Each of the steps mentioned in FIG. 15 will be explained below.

The control point geometrical converter 4001 receives the geometrical conversion information 45 (S401), carries out geometrical conversion of positions of control points, and outputs control point moving magnitude information 4002 to the coordinate geometrical converter 4003 (S402).

The coordinate geometrical converter 4003 obtains the sampling data of the reference image 41 and the floating image 42 (S403 and S404). The coordinate geometrical converter 4003 further arranges a control grid on the obtained floating image 42, obtains control point moving magnitude information 4002 from the control point geometrical converter 4001, and sets positions of the control points in the aforementioned control grid on the basis of the control point moving magnitude information 4002. The coordinate geometrical converter 4003 also carries out coordinate conversion of the coordinates of the sampling points of the reference image 41 by using the control point moving magnitude information 4002 (S405). This step is for calculating coordinates of the image data of the floating image 42 corresponding to the coordinates of the sampling points of the reference image 41. In this example, by performing interpolation of coordinates for coordinate of a certain sampling point on the basis of positions of control points around the sampling point using, for example, the known B-spline function, coordinates of corresponding sampling points in the floating image 42 are calculated.

Then, the coordinate geometrical converter 4003 calculates luminosity value of a sampling point corresponding to each corresponding sampling point of the floating image 42 (sampling point corresponding to each sampling point of the reference image 41) by, for example, linear interpolation calculation (S406). Coordinate (sampling point) of the floating image changed by the movement of the control point and luminosity value at the coordinate (sampling point) are thereby obtained. That is, transformation of the floating image accompanying the movement of the control point is performed in this converter 4003.

The image similarity calculator 4004 obtains luminosity data of the sampling points of the reference image 41, and luminosity data of corresponding sampling points of the geometrically converted floating image 42 (data generated in S405). The image similarity calculator 4004 applies a predetermined evaluation function to the data at these sampling points to calculate the image similarity between the reference image 41 and the floating image 42 (S407). As the image similarity, known mutual information can be used as in the case of the rigid body alignment.

The image similarity maximization part 4005 obtains the image similarity between the reference image 41 and the floating image 42 calculated by the image similarity calculator 4004. In this example, convergence calculation is carried out in order to calculate moving magnitude of each control point that provides the maximum (or local maximum) of the image similarity between the reference image 41 and the floating image 42 (S408). When the image similarity has not converged in the step S408, in order to obtain higher image similarity, the image similarity maximization part 4005 updates the control point moving magnitude information 4002 (S409). Then, the steps S405 to S409 are carried out again by using the updated control point moving magnitude information 4002.

On the other hand, when the image similarity has converged in the step S408, the aligner 40 outputs the obtained control point moving magnitude information 4002 to the floating image transformer 47 (S410). By performing the above processings, the processings of the aligner 40 are completed.

The floating image transformer 47 obtains the floating image 42 and the control point moving magnitude information 4002. The floating image transformer 47 calculates coordinates of all the pixels of the floating image 42 by the same interpolation calculation as that of the step S204 on the basis of the control point moving magnitude information 4002. Then, the floating image transformer 17 calculates luminosity at the obtained coordinates by the same interpolation calculation as that of the step S406 to generate an aligned floating image 48.

According to the embodiment 4, by using the result of the alignment of the ultrasonic blood vessel data and the CT blood vessel data or the result of the rigid body alignment of the ultrasonic volume data and the CT volume data, initial value (position) of a control point used at the time of the alignment between the reference image and the floating image is set. This enables setting of more appropriate initial value of the control grid, and it makes possible to improve the accuracy of the alignment. It is also possible to shorten the time required for the alignment.

By performing the process of the flowchart shown in FIG. 10 using ultrasonic volume data and CT volume data aligned according to the embodiment 4 to obtain a CT image, real time ultrasonograph and CT image can be coincided with high precision. Therefore, high definition matching of both the images is enabled, and a small tumor and so forth can be confirmed with higher accuracy.

DESCRIPTION OF NOTATIONS

21 Ultrasonic volume data acquisitor
22 CT volume data receptor
23 Characteristic data extractor for ultrasonic volume data 24 Characteristic data extractor for CT volume data
25 CT Characteristic data initially rotator
26 Characteristic data aligner
27 Image display
28 Alignment result confirmation and initial rotation redo part

The invention claimed is:

1. An ultrasonic imaging apparatus comprising:
an ultrasound probe that transmits an ultrasonic wave to a subject and receives a ultrasonic wave from the subject;
a position sensor attached to the ultrasound probe;
a memory configured to store a relation of a plurality of predetermined imaging parts of a liver of the subject and a plurality of predetermined rotation angles; and
at least one processor programmed to:
generate an ultrasonograph of the liver of the subject from signals received by the ultrasound probe, and generate first volume data from the ultrasonograph and positional information of the ultrasound probe obtained from the position sensor; and
receive second volume data obtained from imaging the liver of the subject by another external imaging apparatus,
receive a selection of a predetermined imaging part from the plurality of predetermined imaging parts of the liver,
extract first and second characteristic part data, representing a portal vein of the subject, included in each of the first volume data and the second volume data, respectively,
refer to the relation of the plurality of predetermined imaging parts and the plurality of predetermined rotation angles, determine an amount to initially rotate the second characteristic part data in the second volume data and initially rotate the second characteristic part data in the second volume data based on the selected predetermined imaging part,
align the initially rotated second characteristic part data in the second volume data and the first characteristic part data in the first volume data, and
generate an image in which the first characteristic data in the first volume data and the initially rotated second characteristic data in the second volume data are superimposed in alignment.

2. The ultrasonic imaging apparatus according to claim 1, wherein the at least one processor is programmed to:
calculate a rotation angle of the second characteristic part data in the second volume data, and rotate the second characteristic part data in the second volume data by the calculated rotation angle.

3. The ultrasonic imaging apparatus according to claim 1, wherein the at least one processor is programmed to:
receive positional information of the ultrasound probe from the position sensor, and
generate an image from the aligned second volume data at a same position as a position of the ultrasonograph obtained with the ultrasound probe at a position detected by the position sensor.

4. The ultrasonic imaging apparatus according to claim 1, wherein the at least one processor is programmed to generate an image in which the first volume data and the second volume data are superimposed in alignment.

5. The ultrasonic imaging apparatus according to claim 1, wherein the at least one processor is programmed to generate an anatomically defined zone of the liver, and receive a selection of the predetermined imaging part from another plurality of predetermined imaging parts of the generated anatomically defined zone of the liver.

6. The ultrasonic imaging apparatus according to claim 1, wherein the at least one processor is programmed to perform rigid body alignment to align the initially rotated second characteristic part data in the second volume data and the first characteristic part data in the first volume.

7. The ultrasonic imaging apparatus according to claim 1, wherein the at least one processor is programmed to perform non-rigid body alignment to align the initially rotated second characteristic part data in the second volume data and the first characteristic part data in the first volume.

8. An image processing device to process first volume data of a subject from ultrasonic imaging and second volume data of the subject from imaging different from the ultrasonic imaging, the image processing device comprising:
a memory configured to store a relation of a plurality of predetermined imaging parts of a liver of the subject and a plurality of predetermined rotation angles; and
an image processor programmed to:
receive a selection of a predetermined imaging part from among the plurality of predetermined imaging parts of the liver,
extract first and second characteristic part data, representing a predetermined portal vein of the subject, included in each of the first volume data and the second volume data, respectively,
refer to the relation of the plurality of predetermined imaging parts and the plurality of predetermined rotation angles, determine an amount to initially rotate the second characteristic part data in the second volume data and initially rotate the second characteristic part data in the second volume data based on the selected predetermined imaging part,
align the initially rotated second characteristic part data in the second volume data and the first characteristic part data in the first volume data, and
generate an image in which the first characteristic data in the first volume data and the initially rotated second characteristic data in the second volume data are superimposed in alignment.

* * * * *